United States Patent
Briscoe et al.

(10) Patent No.: US 6,218,361 B1
(45) Date of Patent: Apr. 17, 2001

(54) TREATMENT OF CHRONIC ALLOGRAFT REJECTION WITH ANTI-ANGIOGENIC AGENTS

(75) Inventors: David M. Briscoe, Sharon; Karen Moulton, Weston; Mohamed H. Sayegh, Westwood, all of MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 09/200,503

(22) Filed: Nov. 25, 1998

Related U.S. Application Data

(63) Continuation-in-part of application No. 09/195,375, filed on Nov. 18, 1998, now abandoned.

(51) Int. Cl.$^7$ .......................... A61K 38/00; A61K 38/12; A61K 38/13; A61K 31/335; A01N 43/20

(52) U.S. Cl. .............................. 514/11; 514/475

(58) Field of Search ................. 514/11, 2, 885, 514/475

(56) References Cited

U.S. PATENT DOCUMENTS

| | | |
|---|---|---|
| 5,135,919 | 8/1992 | Folkman et al. . |
| 5,639,725 | 6/1997 | O'Reilly et al. . |

OTHER PUBLICATIONS

Roitt et al., Immunology, Gower Medical Publishing, London/NY, p. 24.3, 1985.*
Griffith et al. Chem. Biol., vol. 4, pp. 461–471, 1997.*
Lazary, et al Experientia 24, 1171–1173, 1968.*
Gleich, et al Anticancer Research 4A, 2607–2609, Jul. 1998.*
O'Reilly, et al Cell 79, 315–328, Oct. 1994.*
Hood, et al Immunology 2nd edition, 415–416, 1984.*
Bradley, J.A., Immunology Letters 29 (1–2), 172, 1991.*
Gastl, et al, Oncology 54, 177–184, 1997.*
Roitt, et al Immunology, 24.7, 1985.*
Briscoe, D.M., et al., "Can Human Alloreactive T Cells Initiate Angiogenesis?", *Sixteenth Annual Meeting, American Society of Transplant Physicians*, Abstract 387, May 10–14, 1997.
Ingber D., et al., "Synthetic analogues of fumagillin that inhibit angiogenesis and suppress tumour growth", *Nature*, 348:555–557 (1990).
Adams, D.H., et al., "Chronic Rejection in Experimental Cardiac Transplantation: Studies in the Lewis–F344 Model", *Immunological Reviews*, 134:5–19 (1993).
Minchinton, A.I., "The effect of thalidomide on experimental tumors and metastases", *Anti–Cancer Drugs*, 7:339–343 (1996).

Or, R., et al., "Thalidomide reduces vascular density in granulation tissue of subcutaneously implanted polyvinyl alcohol sponges in guinea pigs", *Experimental Hematology*, 26:217–221 (1998).
Kenyon, B.M., et al., "Effects of Thalidomide and Related Metabolites in a Mouse Corneal Model of Neovascularization", *Exp. Eye Res.*, 64:971–978 (1997).
McCarty, M.F., "Thalidomide may impede cell migration in primates by down–regulating integrin β–chains: potential therapeutic utility in solid malignancies, proliferative retinopathy, inflammatory disorders, neointimal hyperplasia, and osteoporosis", *Medical Hypotheses*, 49:123–131 (1997).
Gutman, M., et al., "Failure of Thalidomide to Inhibit Tumor Growth and Angiogenesis in Vivo", *Anti–Cancer Research*, 16:3673–3678 (1996).
Cole, C.H., et al., "Thalidomide in the management of chronic graft–versus–host disease in children following bone marrow transplantation", *Bone Marrow Transplantation*, 14:937–942 (1994).
Russell, M.E., et al., "Chronic Cardiac Rejection in the LEW to F344 Rat Model", *J. Clin. Invest.*, 97(3):833–838 (1996).
Auerbach, R., and Sidky, Y.A., "Nature of the Stimulus Leading to Lymphocyte–Induced Angiogenesis", *J. of Immunol.*, 123(2):751–754 (1979).
Kaminski, M. and Auerbach, R., "Angiogenesis Induction by CD–4 Positive Lymphocytes (42757)", *Proceedings of the Society for Experimental Biology and Medicine*, 188:440–443 (1988).
Auerbach, R., et al., "Angiogenesis Induction by Tumors, Embryonic Tissues, and Lymphocytes", *Cancer Research*, 36:3435–3440 (1976).
McCarthy, D.M., et al., "Thalidomide for the therapy of graft–versus–host disease following allogeneic bone marrow transplantation", *Biomed. & Pharmacother.*, 43:693–697 (1989).
Saurat, J.–H., et al., "Thalidomide for Graft–versus–Host Disease After Bone Marrow Transplantation", *The Lancet*, Feb. 13:359 (1988).
Lim, S.H., et al., "Successful Treatment with Thalidomide of Acute Graft–Versus–Host Disease After Bone–Marrow Transplantation", *The Lancet*, Jan. 16:117 (1988).
Sidky, Y.A. and Auerbach, R., "Lymphocyte–Induced Angiogenesis: A Quantitive and Sensitive Assay of the Graft–VS.–Host Reaction", *J. of Experimental Medicine*, 141:1084–1100 (1975).

(List continued on next page.)

*Primary Examiner*—Christina Y. Chan
*Assistant Examiner*—Marianne DiBrino
(74) *Attorney, Agent, or Firm*—Nixon Peabody LLP

(57) ABSTRACT

The invention relates a method of inhibiting chronic allograft rejection in a subject with an organ transplant. The method comprises administering an effective amount of one or more anti-angiogenic agents to a subject alone or in combination with one or more immunosuppressive agents. The invention provides new and improved methods of inhibiting allograft rejection.

6 Claims, 2 Drawing Sheets

OTHER PUBLICATIONS

Östraat, Ö, et al., "Moderate additive immunosuppressive effect of thalidomide combined with cyclosporin A in rat cardiac transplantation", *Transplant Immunology*, 4:241–246 (1996).

Battegay, E.J., "Angiogenesis: mechanistic insights, neovascular diseases, and therapeutic prospects", *J. Mol. Med.*, 73:333–346 (1995).

D'Amato, R.J., et al., "Thalidomide is an inhibitor of angiogenesis", *Proc. Natl. Acad. Sci. USA*, 91:4082–4085 (1994).

Denton, M.D., et al., "TNP–470, an Angiogenesis Inhibitor, Interrupts The Development of Graft Arteriosclerosis in a Rat Cardiac Model of Chronic Allograft Rejection", *J. Am. Soc. of Nephrology*, 9:648A (1998).

Ziegler, J., "Angiogenesis Research Enjoys Growth Spurt in the 1990s", *J. Nat. Canc. Inst.* 88:786–788 (1996).

Jenks, S., "Blocking Angiogenesis May Help Keep Tumors Dormant", *J. Nat. Canc. Inst.* 88:787 (1996).

Wells, W.A., "Starving cancer into submission", *Chem. & Biol.*, 5:R87–R88 (1998).

Yatoh, S., et al., "Effect of a Topically Applied Neutralizing Antibody Against Vascular Endothelial Growth Factor on Corneal Allograft Rejection of Rat", *Transplantation*, 66(11):1519–1524 (1998).

Tanaka, H., et al., "Interaction of the Allogeneic State and Hypercholesterolemia in Arterial Lesion Formation in Experimental Cardiac Allografts", *Arteriosclerosis and Thrombosis*, 14(5):734–745(1994).

Sidky, Y.A., and Auerbach, R., "Lymphocyte–Induced Angiogenesis: A Quantitative and Sensitive Assay of the Graft–vs.–Host Reaction", *J. of Experimental Medicine*, 141:1084–1100 (1975).

Auerbach, R., and Sidky, Y.A., "Nature of the Stimulus Leading to Lymphocyte–Induced Angiogenesis", *J. of Immunology*, 123(2):751–754 (1979).

Kaminski, M., and Auerbach, R., "Angiogenesis Induction by CD–4 Positive Lymphocytes[1] (42757)", *Society for Experimental Biology and Medicine*, 188:440–443 (1988).

Torry, R.J., et al., "Vascular Endothelial Growth Factor Expression in Transplanted Human Hearts", *Transplantation*, 60(12):1451–1457 (1995).

Tanaka, H., et al., "Evidence that allogeneic stimuli induce neovascularization in rabbit cardiac allografts", *Annual Meeting of the North American Vascular Biology Organization*, Abstract 391 (1996).

\* cited by examiner

AGM - 1470

US 6,218,361 B1

TREATMENT OF CHRONIC ALLOGRAFT REJECTION WITH ANTI-ANGIOGENIC AGENTS

RELATED APPLICATION

This is a continuation-in-part application of patent application U.S. Ser. No. 09/195,375 filed Nov. 18, 1998, now abandoned, the teachings of which are incorporated herein by reference.

GOVERNMENT SUPPORT

The invention was supported, in whole or in part, by a grants DK 53606 and HL 03518 from the National Institutes of Health. The Government has certain rights in the invention.

BACKGROUND OF THE INVENTION

Acute and chronic allograft rejection are the most common causes of allograft failure. A further understanding and improved treatment of acute and chronic rejection are of critical importance and will optimize transplantation as a successful treatment modality in certain disease states such as kidney and heart failure. The development of chronic rejection is reported to be associated with acute rejection. Indeed, acute allograft rejection episodes are most predictive for the development of chronic rejection. Chronic allograft rejection is a complex multicellular process which generally occurs months to years after organ grafting and is characterized by pathological features such as graft arteriosclerosis. Therefore, additional methods of suppressing acute allograft rejection can also increase the longevity of individuals with organ transplants.

Thus, there is a continued need to develop new and improved methods of inhibiting allograft rejection to promote the quality of life of subjects, such as human transplant patients.

SUMMARY OF THE INVENTION

This invention is based upon the discovery that anti-angiogenic agents inhibit allograft rejection in a subject, such as a mammal. As described herein acute and chronic allograft rejection in subjects with organ transplants are inhibited with anti-angiogenic agents. Thus, the present invention relates to a method of inhibiting allograft rejection in a subject comprising administering an effective amount of one or more anti-angiogenic agents. When the method of the present invention is used to treat acute allograft rejection the anti-angiogenic agent is not thalidomide.

As described herein the anti-angiogenic agent is a substance, such as a polypeptide, peptidomimetic, small organic molecule, sugar or lipid, that interferes, either directly or indirectly, with the development of new blood vessels. These anti-angiogenic agents inhibit allograft rejection. Specifically encompassed by the present invention is a method of treating a subject such as a mammal, including humans, wherein the subject is being treated for chronic allograft rejection. In another aspect of the invention a subject is being treated for acute allograft rejection. In one embodiment the anti-angiogenic agent is angiostatin. In another embodiment the anti-angiogenic agent is endostatin. In preferred embodiments, the anti-angiogenic agent is O-chloroacetylcarbamoyl) fumagillol (referred to herein as AGM-1470), or an analogue of AGM-1470, such as TNP-470. Specifically encompassed by the present invention is a method of inhibiting allograft rejection wherein the subject is being treated for an organ transplant. In preferred embodiment the transplanted organ is a kidney(s) or a heart.

A further embodiment of the present invention is a method of inhibiting allograft rejection wherein the anti-angiogenic agent is co-administered with an effective amount of one or more immunosuppressive agents. Specifically encompassed is a method of treating a subject wherein the subject is being treated for acute allograft rejection by co-administering one or more anti-angiogenic agents and one or more immunosuppressive agents.

The inventions described herein provide alternative and improved methods for the successfully inhibiting, interrupting the development of, or treating established allograft rejection in a subject. The invention thereby offers new and effective methods which are extremely useful in clinical settings for treating mammals, such as humans, following the transplantation of organs such as the heart and kidney.

DETAILED DESCRIPTION OF THE INVENTION

Figure 1:
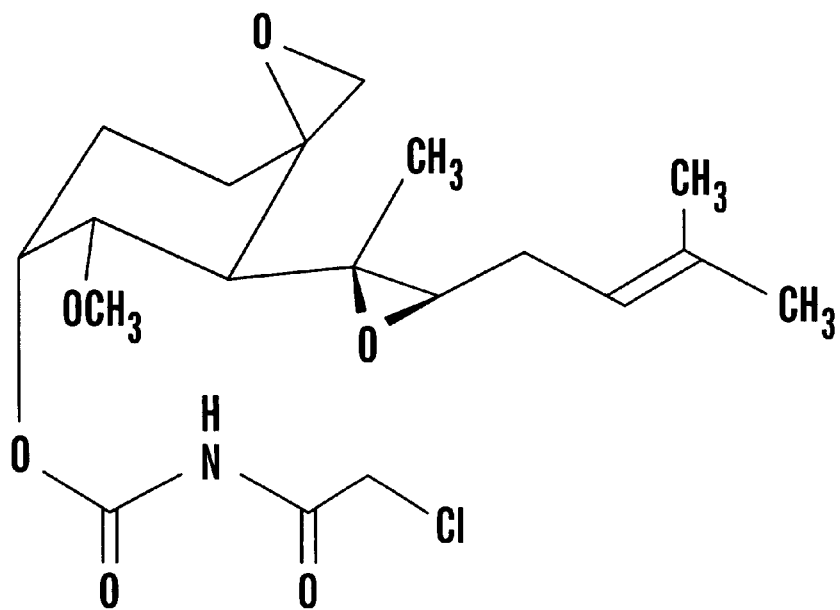
FIG. 1 is the chemical structure of AGM-1470.

The present invention relates to the discovery that acute and chronic allograft rejection can be inhibited by the administration of an effective amount of one or more anti-angiogenic agents, such as angiostatin, endostatin, AGM-1470, or TNP-470, alone or in combination with one or more immunosuppressive agents, such as cyclosporine, FK506, steroids, or antiproliferative agents (e.g., azathioprine, mycophenolate moefitil). Other suitable immunosuppressive agents can be those currently under evaluation in Phase III human clinical trials (e.g., Rapamycin). The methods of the present invention lead to increased graft survival and an accompanying decrease in the mean arteriosclerosis score of blood vessels in transplanted organs.

The term "allograft rejection" refers to a reaction within a transplanted organ or tissue involving both immunologic and non-immunologic responses that ultimately lead to damage or necrosis of some or all of the transplanted organ or tissue. An "organ" refers to a part of the body of a subject exercising a specific function (such as a heart, kidney, liver, or lung). A "tissue" refers to a collection of similar cell types (such as epithelium, connective, muscle and nerve tissue). A "transplanted tissue or organ" is meant to refer to a tissue or organ taken from one subject and implanted into a subject other than the subject from which the organ or tissue was taken.

The phrase "acute allograft rejection" as used herein is intended to refer to a rejection reaction(s) that typically occurs rapidly, within days to weeks after transplantation.

The phrase "chronic allograft rejection" as used herein refers to a rejection reaction(s) that occurs over months to years. Acute and chronic allograft rejection also have unique pathological features. For example, in heart and kidney transplants, chronic allograft rejection is characterized by the proliferation of the smooth muscle cells in the intima of arteries in the graft leading to a graft vascular arteriosclerotic lesion which resembles an accelerated form of arteriosclerosis (Salomon, R. N., et al., *Am. J. Pathol.* 138:791 (1991); Libby, L., et al., *Clinical Transplantation* 8:327 (1994); and Ross, R., *Nature Medicine* 2:527 (1996)). Graft vascular arteriosclerotic lesions in chronic allograft rejection can be determined using well-established criteria as described in Example 2.

The term "anti-angiogenic agent" as used herein is intended to refer to a substance (such as a polypeptide, peptide, small organic molecule, peptidomimetic, sugar, lipid), that interferes, either directly or indirectly, with angiogenesis (e.g., the development of new blood vessels). As used herein "angiogenesis", "endothelial cell proliferation" and the "development of new blood vessels" are equivalent. An anti-angiogenic agent can, for example, directly interact with an endothelial cell by binding, entering or otherwise altering the endothelial cell thereby directly interfering with the formation of blood vessels. Alternatively or additionally, the anti-angiogenic agent can act indirectly by, for example, binding, entering or otherwise altering a cell other than an endothelial cell (e.g., a T-cell) thereby indirectly interfering with angiogenesis by, for example, altering the production, secretion or processing of other factors (e.g., vascular growth factors such as VEGF, β-FGF, TNF-α, TNF-β) involved in angiogenesis. Graft-infiltrating T-cells and macrophages, for example, result in smooth muscle cell proliferation (e.g., the smooth muscle of the intimal wall of arteries in transplant organs) and graft arteriosclerosis (Tullius, S. G., et al., *Transplantation* 59:313 (1995)). Thus, the anti-angiogenic agents of the present invention can decrease the number of blood vessels through which the infiltrating T-cells and macrophages migrate to the graft. Alternatively and additionally, the anti-angiogenic agents described herein can alter the ability of infiltrating T-cells and macrophages to mediate the process of arteriosclerosis. In either case allograft rejection is inhibited. Methods to assess anti-angiogenic activity of a substance are routine and well-known to one of skill in the art and include, for example, inhibition of angiogenesis in a chicken chorioallantoic membrane assay or a rabbit cornea micropocket assay (See, for example, Ingber, D., et al., *Nature* 348:555–557 (1990); O'Reilly, M. S., et al., *Cell* 79:315 (1994); Folkman, J., *New Eng J. Med* 333:1757 (1995); Holmgren, L., et al., *Nature Medicine* 1:149 (1995); O'Reilly, M. S., et al., *Cell* 88:277 (1997); and O'Reilly, M. S., et al., U.S. Pat. No. 5,639,725).

Where the anti-angiogenic agent is a polypeptide, the polypeptide can be post-translationally modified (e.g., amidated, demethylated, glycosylated or phosphorylated). Anti-angiogenic agents that are polypeptides can be, for example, endostatin, or angiostatin, or both.

In a preferred embodiment the anti-angiogenic agent, alone or when co-administered with an immunosuppressive agent, is used to inhibit the allograft rejection of a subject wherein the subject has undergone an organ transplant. Specifically encompassed by the present invention is the administration of one or more anti-angiogenic agents, alone or when co-administered with immunosuppressive agents, to inhibit the rejection of heart or kidney transplants.

The phrase to "inhibit allograft rejection" as used herein is meant to refer to suppressing, diminishing, limiting, decreasing, reducing, preventing, retarding, or slowing down allograft rejection. Indices to determine inhibition of allograft rejection are well known to one of skill in the art and include improvement in pathologic, clinical and biochemical criteria of rejection as well as overall function of the allograft (Suki, N., *"Primer on Transplantation"*, American Society of Transplantaion Physicians, New York, N.Y. (1998)). For example, indices of improving chronic allograft rejection can be increased graft survival rates and decreased arteriosclerosis score of blood vessels to the allograft organ (See Examples 1 and 2).

The invention also pertains to inhibiting or interrupting the development of an allograft rejection by administering one or more anti-angiogenic agents, alone or in combination with one or more immunosuppressive agents. The treatment of established allograft rejection with the methods described herein are also within the scope of the invention.

In one embodiment of the present invention the anti-angiogenic agents are the polypeptides angiostatin and endostatin. The anti-angiogenic activity of endostatin and angiostatin are well documented and have been used to successfully inhibit the development of new blood vessels to tumors. See, for example, O'Reilly, M. S., et al., *Cell* 79:315 (1994); Folkman, J., *New Eng J. Med* 333:1757 (1995); Holmgren, L., et al., *Nature Medicine* 1:149 (1995); O'Reilly, M. S., et al., *Cell* 88:277 (1997); and O'Reilly, M. S., et al., U.S. Pat. No. 5,639,725, the teachings of which are incorporated herein in their entirety.

In another embodiment, the anti-angiogenic agent is AGM-1470 (FIG. 1), or an analogue of AGM-1470 such as TNP-470. The anti-angiogenic activity of AGM-1470 and TNP-470 is known. See, for example, Ingber, D., et al., *Nature* 348:555 (1990); Antoine, N., et al., *Am. J. Pathol.* 148:393 (1996); and Griffith, E., et al., *Chem. Biol.* 4:461 (1997); Folkman, J., et al., U.S. Pat. No. 5,135,919 (1992), the teachings of which are incorporated herein in their entirety. TNP-470 inhibits DNA synthesis in endothelial cells by inhibiting growth factor activation of cyclin dependent kinases (Koyama, H., et al., *Circulation Res.* 79:757 (1996)) as well as other enzymatic pathways (Antoine, N., et al., *Am. J. Pathol.* 148:393 (1996); and Griffith, E., et al., *Chem. Biol.* 4:461 (1997)).

Figure 2:
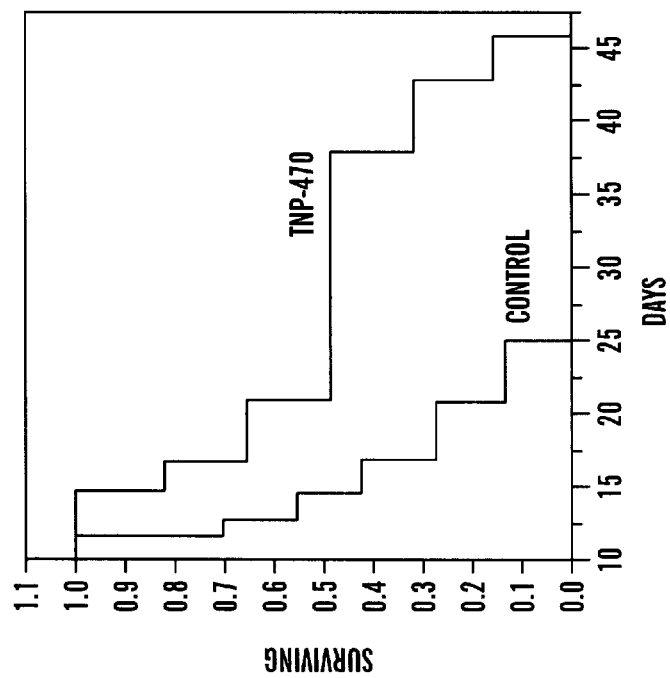
FIG. 2 is a graph depicting the fraction or percent of allografts which survive (surviving) over time in days (Days) from Fisher strain rats ("F344 rats") transplanted with hearts from Lewis strain rats ("LEW strain") in an acute allograft rejection model. Transplant recipients were treated with TNP-470 or received no treatment (control).

TNP-470 inhibits acute and chronic allograft rejection (Examples 1 and 2). The 30 day graft survival rate of rat heart transplant recipients increased from 0% to greater than 50% when allograft recipients were treated with the anti-angiogenic agent TNP-470 (Example 1; FIG. 2). Thus, TNP-470 suppresses acute allograft rejection.

Figure 3:
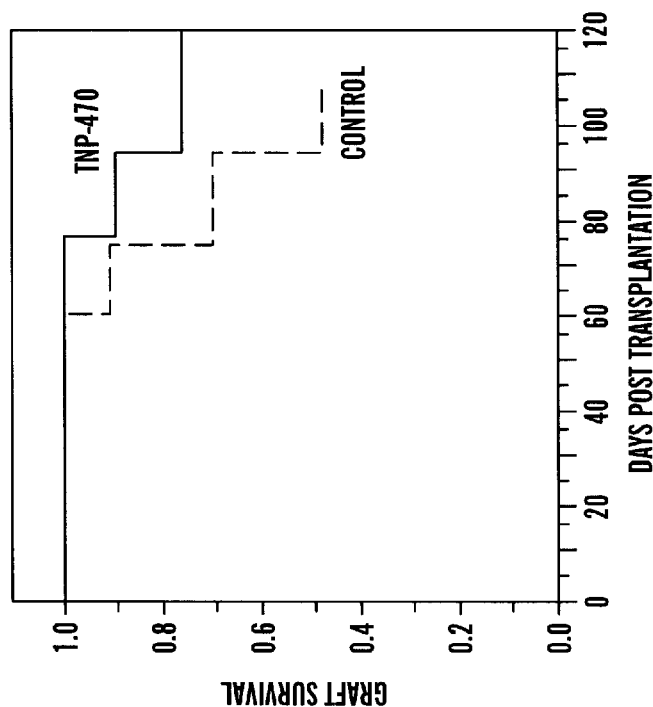
FIG. 3 is a graph depicting the fraction or percent of allografts which survived (Graft Survival) over time in days (Days Post Transplantation) from F344 rats transplanted with hearts from LEW rats in a chronic allograft rejection model. Following treatment with the immunosuppressive agent cyclosporine, the F344 rats were treated with the anti-angiogenic agent TNP-470 or vehicle as a control.

TNP-470 can also suppress chronic allograft rejection (Example 2; FIG. 3). A 120 day increased graft survival rate occurred when transplant recipients were treated with TNP-470 for days 30–120 after allografting, following an initial 30 days of treatment with cyclosporine, than recipients who received only cyclosporine for 30 days (approximately 75% survival rate in cyclosporine/TNP-470 treated recipients compared with approximately 45% in cyclosporine alone treated recipients; Example 2; FIG. 3). In addition, TNP-470 treatment ameliorated the characteristic graft arteriosclerotic lesions manifested in chronic allograft rejection (Example 2). Decreased occlusion of cardiac vessels after 120 days was observed in cyclosporine/TNP-470 treated animals (Example 2). Thus, TNP-470 suppresses chronic allograft rejection.

In another aspect of the invention analogues of AGM-1470 (Griffith, E., et al., *Chem. Biol.* 4:461 (1997)), such as TNP-470 (Ingber, D., et al., *Nature* 348:555 (1990)), can be used to inhibit allograft rejection. "Analogue" refers to a compound that resembles AGM-1470 in structure (e.g., chemical structure), yet inhibits allograft rejection as described herein for anti-angiogenic agents.

Experimental methods to produce and purify the anti-angiogenic agents of the present invention (e.g., angiostatin or endostatin) are known to one of skill in the art. These techniques include the production of recombinant angiostatin and endostatin which have previously been shown to be anti-angiogenic when produced in host cells such as yeast (such as *Pichia pastorius* or *Saccharomyces cerevisa*), bacteria (such as *Escherichia* or *Bacillus*) expression systems; animal cells or tissue, including insect (such as baculoviruses) or mammalian cells (such as somatic or embryonic cells, Chinese hamster ovary cells, HeLa cells, human 293 cells and monkey COS-7 cells). Appropriate vectors, transfection and transformation protocols to generate recombinant anti-angiogenic agents are well-known to the skilled artisan. Exemplary discussions of recombinant DNA technologies can be found in, for example, Ausubel, et al., "*Current Protocols in Molecular Biology*", John Wiley & Sons, Inc., (1998). Nucleic acid molecules coding for suitable anti-angiogenic agents (e.g., angiostatin and endostatin), in several mammalian species (e.g., mouse, human, rhesus monkey, pigs, cows), are known in the art and can be obtained from, for example, the EMBL/GenBank data bases. For example, the Accession numbers for angiostatin are 148501, 148503, 148504, 148505. Alternatively, other sequences can be employed, such as related genes which encode structurally or functionally equivalent polypeptides to anti-angiogenic agents described herein. The related genes and the polypeptides encoded by the related genes can share structural (e.g., nucleotide, or amino acid sequence, or three dimensional structure) or activity (e.g., inhibit allograft rejection) similarities to polypeptide anti-angiogenic agents described herein (e.g., angiostatin, endostatin).

Related genes can encode functionally equivalent polypeptides which inhibit allograft rejection as described for the anti-angiogenic agents of the present invention. For example, functionally equivalent polypeptides can increase graft survival rates (Examples 1 and 2; FIGS. 2 and 3), or decrease mean arteriosclerosis score of blood vessels in the allograft (Example 2), or both.

Thus, polypeptides or peptides which are structurally or functionally equivalent to known polypeptide or peptide anti-angiogenic agents (e.g., angiostatin, endostatin) can be used in the methods of the present invention. Such polypeptides can show nucleic acid or amino acid sequence identity with the anti-angiogenic agents described herein (e.g., angiostatin, endostatin). In one embodiment structurally equivalent anti-angiogenic agents share at least about 40% sequence identity (nucleic acid or amino acid identity) with the corresponding native sequence, preferably, at least about 50–60% sequence. In a more preferred embodiment, the percent sequence identity is at least about 65–75%, and still more preferably, at least about 80%.

Methods to determine the identity of structurally equivalent polypeptides by sequence identity are routine and familiar to one of skill in the art. Nucleic acid or amino acid sequence identity can be determined using database search strategies well known in the art including, for example, Basic Local Alignment Search Tool (BLAST) (Altschul, S. F., et al., *J. Mol. Biol.* 215:403–410 (1990)) and FASTA (Pearson, W. R., et al., *Proc. Natl. Acad. Sci. U.S.A.* 85:2444–2448 (1988)) algorithms. Structurally equivalent nucleic acids, including DNA or RNA, can also be detected and/or isolated by specific hybridization (e.g., under high stringency conditions). "Stringency conditions" for hybridization is a term of art which refers to the conditions of temperature, salt and buffer concentrations which permit hybridization of a particular nucleic acid to a second nucleic acid. "High stringency conditions", "moderate stringency conditions", and "low stringency conditions" for nucleic acid hybridizations are explained on pages 2.10.1–2.10.16 and pages 6.3.1–6.4.10 in *Current Protocols in Molecular Biology* (Ausubel, F. M. et al., "*Current Protocols in Molecular Biology*", John Wiley & Sons, (1998)) the teachings of which are hereby incorporated by reference.

It is also envisioned that biologically active fragments of the polypeptide anti-angiogenic agents described herein can be used to inhibit allograft rejection. The term "fragment" is intended to encompass a portion of the anti-angiogenic agent; or, in the case of a polypeptide anti-angiogenic agent, a nucleic acid molecule or sequence encoding an anti-angiogenic polypeptide which is at least approximately 25 contiguous nucleotides to at least approximately 50 contiguous nucleotides or longer in length. "Nucleic acid molecule" is meant to refer to chains of nucleotides joined together by phosphodiester bonds to form nucleic acid sequences. The nucleic acid molecules can be double stranded or single stranded and can be deoxyribonucleotide (DNA) molecules, such as cDNA or genomic DNA, or ribonucleotide (RNA) molecules. The anti-angiogenic activity of such fragments can be determined using techniques well-known to the skilled artisan (O'Reilly, M. S., et al., *Cell* 79:315 (1994); Folkman, J., *New Eng J. Med* 333:1757 (1995); Holmgren, L., et al., *Nature Medicine* 1:149 (1995); O'Reilly, M. S., et al., *Cell* 88:277 (1997); and O'Reilly, M. S., et al., U.S. Pat. No. 5,639,725). The ability of fragments of anti-angiogenic agents to inhibit allograft rejection can also be determined using routine, art-recognized criteria and methods described herein including, for example, graft survival rates and arteriosclerosis scores of blood vessels of the allografts. (See Examples 1 and 2; and Russell, M. E., et al., *J. Clin. Invest.* 97:833 (1996)).

In another aspect of the invention, peptidomimetics (molecules which are not polypeptides, but which mimic aspects of their structures to bind to the same site), that are based upon the polypeptide anti-angiogenic agents of the present invention (e.g., angiostatin, endostatin) which can inhibit allograft rejection in a similar manner (e.g., increased survival rate or decreased mean arteriosclerosis score as discussed in Examples 1 and 2), can also be used as anti-angiogenic agents.

The proteins, polypeptides and peptides of the present invention can comprise naturally-occurring amino acids (e.g., L-amino acids), non-naturally-occurring amino acids (e.g., D-amino acids), and small molecules that biologically mimic the anti-angiogenic polypeptides or peptides, and are referred to herein as peptide analogs, derivatives or mimetics (Saragovi, H. U., et al., *BioTechnology,* 10:773–778 (1992)). The protein, polypeptide, peptidomimetic of the present invention can be in a linear or cyclic conformation.

The anti-angiogenic agents of the present invention can comprise either the 20 naturally occurring amino acids or other synthetic amino acids. Synthetic amino acids encompassed by the present invention include, for example, naphthylalanine, L-hydroxypropylglycine, L-3,4-dihydroxyphenylalanyl, α-amino acids such as L-α-hydroxylysyl and D-α-methylalanyl, L-α-methyl-alanyl, β amino-acids such as β-analine, and isoquinolyl.

D-amino acids and other non-naturally occurring synthetic amino acids can also be incorporated into the anti-angiogenic agents of the present invention. Such other non-naturally occurring synthetic amino acids include those where the naturally occurring side chains of the 20 genetically encoded amino acids (or any L or D amino acid) are replaced with other side chains, for instance with groups such as alkyl, lower alkyl, cyclic alkyl, amide, hydroxy, carboxy, lower alkyl carboxylic acid ester, sulfonic acid, a lower alkyl sulfonic acid ester or a phosphorous acid or ester thereof.

These peptide mimetics possess biological activity (e.g., anti-angiogenic activity) similar to the biological activity of the corresponding polypeptide or peptide compound (e.g., angiostatin, endostatin), but can possess a "biological advantage" over the corresponding polypeptide or peptide anti-angiogenic agent with respect to one, or more, of the following properties: solubility, stability, and susceptibility to hydrolysis or proteolysis.

Methods for preparing peptide mimetics include modifying the N-terminal amino group, the C-terminal carboxyl group, and/or changing one or more of the amino linkages in the peptide to a non-amino linkage. Modifications of peptides to produce peptide mimetics are described in U.S. Pat. Nos: 5,643,873 and 5,654,276, the teachings of which are incorporated herein by reference. The anti-angiogenic agents can also be cyclic peptide mimetics. Such cyclic test substances can be produced using known laboratory techniques (e.g., as described in U.S. Pat. No: 5,654,276, the teachings of which are herein incorporated in their entirety by reference).

These peptidomimetic compounds can be manufactured by art-known and art-recognized methods. Determining an appropriate chemical synthesis route for the peptide mimetics can generally be readily identified using no more than routine skill.

The anti-angiogenic agents of the present invention can be synthesized using standard laboratory methods that are well-known to those of skill in the art, including standard solid phase techniques. Anti-angiogenic agents comprising polypeptides of naturally occurring amino acids (e.g., angiostatin, endostatin) can also be produced by recombinant DNA techniques known to those of skill.

Anti-angiogenic agents can also be small organic molecules, for example, molecules with a molecular weight less than about 1000 atomic mass units (amu), with the proviso that the anti-angiogenic agent is not thalidomide when acute allograft rejection is being treated. In one aspect, the small organic molecule has a molecular weight between about 275 and about 1000 amu.

Thus, it is to be understood that the method of inhibiting allograft rejection described herein can be performed with anti-angiogenic agents other than those specifically described herein. As such, anti-angiogenic agents not yet discovered can also be used in this method of treatment, once it has been determined that the agent is anti-angiogenic (e.g., inhibits or suppresses the formation of new blood vessels) and inhibits allograft rejection. These anti-angiogenic agents are also within the scope of the present invention.

The method of the present invention can be used to inhibit allograft rejection in a subject with transplanted solid organs or tissues. Examples of solid organs include heart, kidney, lungs, stomach, pancreas, liver, intestines, esophagus, and skin. Examples of tissues include bone marrow, corneas. The method of the present invention is especially useful for suppressing allograft rejection of transplanted heart and kidneys. It is also envisioned that the methods of the invention can be used to inhibit rejection of transplanted limbs in a subject.

An "effective amount" is the quantity of an anti-angiogenic agent which results in a longer life expectancy for subjects with an organ or tissue transplant compared with subjects who did not undergo the treatment. Alternatively or additionally, "an effective amount" is the quantity of an anti-angiogenic agent which results in a decreased manifestation or inhibition, or reversal of pathological and/or the symptoms of allograft rejection, such as those which prolong allograft survival, compared with subjects who did not undergo the treatment. In the case of chronic allograft rejection, improvements in graft arteriosclerosis scores (Example 2) can indicate an effective amount of an anti-angiogenic agent.

It will be appreciated that the actual effective amount of an anti-angiogenic agent in a specific case to inhibit allograft rejection can vary according to the specific anti-angiogenic agent being utilized, the particular composition formulated, the mode of administration, the type of organ or tissue transplant and on the characteristics of the subject, such as general health, age, sex, body weight and tolerance to drugs. Dosages for a particular subject can be determined by one of skill in the art using conventional considerations (e.g., by means of appropriate, conventional pharmacological protocol). Typically, an effective amount of the anti-angiogenic agents can range from about 1 mg per kilogram body weight per day to about 1000 mg per kilogram body weight per day for an adult. Preferably, the dosage ranges from about 1 mg per kilogram body weight per day to about 100 mg per kilogram body weight per day.

A "subject" is preferably a mammal. The term "mammals", as defined herein, refers to any vertebrate animal, including monotremes, marsupials and placental, that suckle their young and either give birth to living young (eutherian or placental mammals) or are egg-laying (metatherian or nonplacental mammals). Examples of mammalian species include primates (e.g., humans, monkeys, chimpanzees, baboons), rodents (e.g., rats, mice, guinea pigs, hamsters), companion animals (e.g., dogs, cats), ruminants (e.g., cows, horses) and monogastric farm animals (e.g., pigs).

An anti-angiogenic agent can be co-administered to a subject with other pharmacologically active agents; for example, with other immunosuppressive agents used to suppress allograft rejection. The term "immunosuppressive agent" as used herein is meant to refer to any substance (e.g., polypeptide, peptide, peptidomimetic, small organic molecule, sugar, lipid) which inhibits or prevents the development of an immunological response. "Co-administration" as used herein is intended to refer to the administration of both an anti-angiogenic agent and an immunosuppressive agent either simultaneously or in sequence. Co-administration can result in synergistic or additive effects of either the anti-angiogenic agent alone or the immunosuppressive agent alone in preventing allograft rejection. For example, the anti-angiogenic agent can be administered to the subject at the same time as the immunosuppressive agent or prior to or after the administration of the immunosuppressive agents. The immunosuppressive agent can be, for example, cyclosporin, or FKS06, or steroids, or antiproliferative agents (such as azathioprine, mycophenolate moefitil), or any combination thereof. Other suitable immunosuppressive agents can also be those currently under evaluation in Phase III human clinical trials (e.g., Rapamycin).

In the methods of the present invention, anti-angiogenic agents can be formulated into compositions with an effective amount of the anti-angiogenic agent as the active ingredient. Such compositions can also comprise a pharmaceutically acceptable carrier, and are referred to herein as pharmaceutical compositions. The anti-angiogenic agent compositions of the present invention can be administered intramuscularly, subcutaneously, intraperitoneally, intravenously, parenterally, orally, nasally, by inhalation, by implant, by injection, or by suppository. Anti-angiogenic agents which resist proteolysis can be administered orally, for example, in capsules, suppositories, suspensions or tablets. For example, the anti-angiogenic agents angiostatin, endostatin, AGM-1470 and TNP-470, are preferably administered subcutaneously. The anti-angiogenic agent composition can be administered in a single dose or in more than one dose over a period of time to achieve a level of inhibition which is sufficient to confer the desired effect.

Anti-angiogenic agents in pharmaceutical compositions are administered to the individual in conjunction with an acceptable pharmaceutical carrier. Suitable pharmaceutical carriers may contain inert ingredients which do not interact with the anti-angiogenic agent. Standard pharmaceutical formulation techniques may be employed such as those described in Remington's Pharmaceutical Sciences, Mack Publishing Company, Easton, Pa. Suitable pharmaceutical carriers include, but are not limited to sterile water, physiological saline, bacteriostatic saline (saline containing about 0.9% mg/ml benzyl alcohol), other saline solutions (such as Ringer's-lactate solution, Hank's solution, phosphate-buffered saline), alcohols, polyethylene glycols, gelatin, carbohydrates such as lactose, amylose or starch, magnesium stearate, talc, silicic acid, viscous paraffin, fatty acid esters, hydroxymethylcellulose, or polyvinyl pyrolidone. Methods for encapsulating compositions (such as in a coating of hard gelatin or cyclodextran) are known in the art (Baker, et al., *Controlled Release of Biological Active Agents*, John Wiley and Sons, 1986). The pharmaceutical preparations can be sterilized and desired, mixed with auxiliary agents, e.g., lubricants, preservatives, stabilizers, wetting agents, emulsifiers, salts for influencing osmotic pressure, buffers, coloring, and/or aromatic substances and the like which do not deleteriously react with the anti-angiogenic agents. The anti-angiogenic agents can also be combined where desired with other active substances, e.g., enzyme inhibitors, to reduce metabolic or proteolytic degradation.

For parenteral application, particularly suitable are injectable, sterile solutions, preferably oily or aqueous solutions, as well as suspensions, emulsions, or implants, including suppositories. Ampules are convenient unit dosages.

The following Examples are offered for the purpose of illustrating the present invention and are not to be construed to limit the scope of this invention. The teachings of all references cited herein are hereby incorporated by reference.

EXAMPLE 1

Suppression of Acute Allograft Rejection in Rat Models

The Lewis strain (hereinafter "LEW") (Harlan Sprague Laboratories) and Fisher strain (hereinafter "F344") (Harlan sprague Laboratories) of rats were used to study acute and chronic rejection. Procedures for transplantation of organs (e.g., heart, kidney) and techniques to evaluate organ and animal survival as well as criteria to score indices of graft rejection such as arteriosclerosis are routine, well established and art-recognized described by, for example, Adams, D. H., et al., *Immunol. Rev.* 134:5 (1993); Tilney, N. L., et al., *Transplant Proc.* 25:861 (1993); Nadeau, K. C., et al., *Proc. Natl. Acad. Sci. USA* 92:8729 (1995); Russell, M. E., et al., *J. Clin. Invest.* 97:833 (1996); and Azuma, H., et al., *Proc. Natl. Acad. Sci. USA* 93:12439 (1997), the teachings of which are incorporated herein in their entirety.

F344 recipient rats underwent heterotopic abdominal transplantation of hearts from LEW rats. Following surgery, one group of allograft recipients was treated with a subcutaneous injection of 20 mg/kg TNP-470, dissolved in sterile saline, every other day for 30 days. A control group received no treatment.

Transplant recipients were monitored for graft survival by external palpation of the transplant heart. A palpable heartbeat was indicative of graft survival. The result of TNP-470 treatment on survival of transplant recipients is depicted in FIG. 2. Greater than 50% of grafts from TNP-470 treated animals survived for at least approximately 22 days and as long as approximately 37 days, whereas acute graft rejection developed in all of the controls animals. None of the cardiac grafts from control animals survived 25 days. In this animal model, typically grafts fail due to acute allograft rejection within the first 3 weeks (Adams, D. H., et al., *Immunol. Rev.* 134:5 (1993); and Russell, M. E., et al., *J. Clin. Invest.* 97:833 (1996)). These results show that TNP-470 suppresses acute allograft rejection.

EXAMPLE 2

Suppression of Chronic Allograft Rejection In Rat Models

Cyclosporine treatment can prevent the initial acute allograft rejection and facilitate long term engraftment (Nadeau, K. C., et al., *Proc. Natl. Acad. Sci. USA* 92:8729 (1995); Azuma, H., et al., *Proc. Natl. Acad. Sci. USA* 93:12439 (1997)). However, once cyclosporine treatment is discontinued, animals typically develop progressive chronic allograft rejection (Russell, M. E., et al., *J. Clin. Invest.* 97:833 (1996)). Rats undergoing chronic allograft rejection develop moderate lymphocyte as well as monocyte and macrophage infiltrates in the interstitium and perivascular space in association with arteriovascular lesions in the allograft (Adams, D. H., et al., *Immunol. Rev.* 134:5 (1993); Tilney, N. L., et al., *Transplant Proc.* 25:861 (1993); Russell, M. E., et al., *J. Clin. Invest.* 97:833 (1996); and Azuma, H., et al., *Proc. Natl. Acad. Sci. USA* 93:12439 (1997)). This characteristic arteriovascular lesion begins as early as day 7–14. In the early phase of chronic allograft rejection (between 28 and 75 days after organ transplantation), the intima of blood vessels in the graft thickens primarily as a result of macrophage accumulation and smooth muscle cell proliferation. In the later phase of chronic allograft rejection (between 90 and 120 days after organ transplantation), smooth muscle cell proliferation in vessels of the graft is very pronounced and the arteriovascular lesion becomes characteristic of chronic allograft rejection. Accumulation of macrophages and the activation of local macrophages is critical in the development of this phase of chronic allograft rejection in this animal model.

F344 recipient rats which had undergone heterotopic abdominal transplantation of hearts from LEW rats were used as a model for studying the effect of the co-administration of TNP-470 (an anti-angiogenic agent) and cyclosporine (an immunosuppressive agent) in inhibiting chronic allograft rejection.

F344 transplant recipient rats were divided into three groups (Prevention, Therapeutic and Interruption Groups). Cyclosporine (5 mg/kg/day) and TNP-470 (20 mg/kg/every other day) were administered subcutaneously. The "Prevention Group" (or "Control Group") was treated for 30 days with cyclosporine alone and then received no additional treatment for days 30–120 following grafting. Animals in the "Therapeutic Group" were treated with cyclosporine for 30 days after surgical transplantation to prevent acute allograft rejection followed by treatment with TNP-470 until day 120 after grafting. Animals in the "Interruption Group" did not receive any treatment for 30 days (to develop acute allograft rejection); after which they were treated with TNP-470 from days 30–120 following graft transplantation. The Therapeutic Group is particularly applicable for the treatment of allograft rejection in humans.

Grafts were monitored for survival by palpation to detect a heartbeat and analyzed histologically using well-established methods (Russell, M. E., et al., *J. Clin. Invest.* 97:833 (1996); and Azuma, H., et al., *Proc. Natl. Acad. Sci. USA* 93:12439 (1997)). The results for this study are depicted in FIG. 3. In addition, cardiac grafts were harvested from recipients, fixed in 10% buffered formalin, embedded in paraffin and analyzed morphologically to assess the graft and the degree of occlusion of the arterial lumen (e.g., an arteriosclerosis score). Methods for tissue harvesting and analysis are well-known, routine and familiar to one of ordinary skill in the art.

In the Control Group, animals were treated with a short course of cyclosporine for 30 days. Cyclosporine was then discontinued for 90 additional days. Analysis of the grafts from animals in the Control Group revealed chronic allograft rejection and occlusion of blood vessels in the cardiac graft (FIG. 3). In the Interruption Group, administration of TNP-470 for the last 90 days inhibited the development of chronic rejection and increased graft survival (FIG. 3—approximately 75% survival at day 120 for the Interruption Group versus approximately 45% survival for the Control Group) and improved arteriosclerosis scores of allografts (2.06±0.58 (n=5) for the Control Group versus 0.96±0.14 (n=10) for the Interruption Group). An arteriosclerosis score of 0 indicates 0% occlusion of the cardiac vessels; 1 indicates 20% occlusion; 2 indicates 40% occlusion; 3 indicates 60% occlusion; 4 indicates 80% occlusion; and 5 indicates 100% occlusion.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A method of inhibiting chronic allograft rejection in a subject with an organ transplant comprising the step of administering an effective amount of an anti-angiogenic agent selected from the group consisting of AGM 1470 and TNP-470.

2. The method of claim 1 wherein the anti-angiogenic agent is AGM 1470.

3. The method of claim 1 wherein the anti-angiogenic agent is TNP-470.

4. The method of claim 1 wherein the transplanted organ is a kidney or heart.

5. The method of claim 1 wherein the anti-angiogenic agent is co-administered with an effective amount of one or more immunosuppressive agents.

6. The method of claim 5 wherein the immunosuppressive agent is cyclosporine.

\* \* \* \* \*

UNITED STATES PATENT AND TRADEMARK OFFICE
CERTIFICATE OF CORRECTION

PATENT NO. : 6,218,361 B1
APPLICATION NO. : 09/200503
DATED : April 17, 2001
INVENTOR(S) : David M. Briscoe, Karen Moulton and Mohamed H. Sayegh It is certified that error appears in the above-identified patent and that said Letters Patent is hereby corrected as shown below:

Col. 1 lines 12-15 should read,

GOVERNMENT SUPPORT

The invention was supported, in whole or in part, by grants DK053606, HL03518, AI034965 and AI040629 awarded by the National Institutes of Health. The Government has certain rights in the invention.

Signed and Sealed this

Twenty-fifth Day of May, 2010

David J. Kappos
*Director of the United States Patent and Trademark Office*